(12) United States Patent
Hudson

(10) Patent No.: US 6,987,563 B2
(45) Date of Patent: Jan. 17, 2006

(54) LUMINESCENSE VALIDATION MICROPLATE

(76) Inventor: Gordon S. Hudson, 3200 Neuse Banhs Ct., Wake Forest, NC (US) 27587

( * ) Notice: Subject to any disclaimer, the term of this patent is extended or adjusted under 35 U.S.C. 154(b) by 0 days.

(21) Appl. No.: 11/106,091

(22) Filed: Apr. 14, 2005

(65) Prior Publication Data

US 2005/0231714 A1 Oct. 20, 2005

Related U.S. Application Data

(60) Provisional application No. 60/561,854, filed on Apr. 14, 2004.

(51) Int. Cl.
*G01N 1/10* (2006.01)
*G01N 1/00* (2006.01)

(52) U.S. Cl. .................. 356/246; 356/244; 436/174; 422/82.05

(58) Field of Classification Search ............... 356/244, 356/246, 317–319; 250/459.1, 491.1; 436/174, 436/164, 43; 422/63–65, 82.05, 82.08
See application file for complete search history.

(56) References Cited

U.S. PATENT DOCUMENTS

| | | | | | |
|---|---|---|---|---|---|
| 4,772,453 | A | * | 9/1988 | Lisenbee | 422/52 |
| 5,100,804 | A | * | 3/1992 | Brunelle et al. | 436/126 |
| 5,290,513 | A | * | 3/1994 | Berthold et al. | 422/52 |
| 5,784,152 | A | * | 7/1998 | Heffelfinger et al. | 356/73 |
| 6,071,748 | A | * | 6/2000 | Modlin et al. | 436/174 |
| 6,310,687 | B1 | * | 10/2001 | Stumbo et al. | 356/317 |
| 6,335,997 | B1 | * | 1/2002 | Lee et al. | 385/140 |
| 6,597,450 | B1 | * | 7/2003 | Andrews et al. | 356/317 |
| 6,835,574 | B2 | * | 12/2004 | Neilson et al. | 436/149 |
| 2004/0061852 | A1 | * | 4/2004 | Wulf et al | 356/243.1 |

* cited by examiner

*Primary Examiner*—Gregory J. Toatley, Jr.
*Assistant Examiner*—Sang H. Nguyen
(74) *Attorney, Agent, or Firm*—Passé Intellectual Property; James Passé

(57) ABSTRACT

A luminescence validation microplate for testing the validity of a luminescence microplate reader is provided which can efficiently and cost-effectively test luminescence microplate readers with a series of tests to determine linearity, alignment, reproducibility and cross talk all on the same plate with improved results.

8 Claims, 4 Drawing Sheets

LUMINESCENSE VALIDATION MICROPLATE

This application claims priority of provisional application Ser. No. 60/561,854 filed Apr. 14, 2004.

BACKGROUND OF THE INVENTION

1. Filed of the Invention

The present invention relates to the measurement of luminescence by a luminescence microplate reader. In particular, the present invention relates to a luminescence validation microplate which is used to validate the reliability of the information received from a luminescence assay microplate during its reading in a luminescence microplate reader.

2. Description of Related Art

The growth of biological research, reporter gene assays and new pharmaceutical compound screening and in some cases medical diagnostics has created a need for handling large numbers of test samples at one time in order to control costs and efficiently handle these large numbers of samples. A number of analytical methods are now available for high throughput screening of these samples. One of those important methods which are in increasing use is the use of luminescence. It has been discovered that various substrates both naturally occurring in nature and man-made have luminescence properties at a given wavelength and can be used as a tag or marker for various test assays where luminescence can be used as a direct measure of some other activity movement or the like. Often called luminophors these compositions are readily available in various wavelengths intensities and utilities. Techniques for using with these substrates are similar to fluorescence emission and radioactive measurement techniques. Typically, large numbers of samples are processed for luminescence emission in a multi-well sample plate called an assay microplate. These microplates are typically rectangular and provide an array of wells, usually 24 or 96 wells in typical examples, but 384 well and 1536 well microplates are becoming more common as well. Most common plates are 96 well (in 8 by 12 configuration) at this time and all plates regardless of the number of wells, comprise roughly the same rectangular size. While originally variations that were significant existed between manufacturers of these plates requiring plates matching the reader, new standards promulgated by SBS/NIST now exist standardizing not only the rectangular size of the plates but the position and size of the wells for the various multi-well configurations. New standards allow for manufacture of microplates which fit all manufacturers' machines and allow for a reduction in problems associated with their use. Notable, as well numbers per plate increase, well diameter decreases and these standardizations have become even more critical.

Assay microplate wells are filled with test samples and then placed in a detector system of the luminescence microplate reader, for measuring the relative luminescence emissions of each test well. Since different luminescence materials use for microplates assays produce different degrees of light intensity. Light intensity can a direct measure of test results, i.e. the greater the light intensity the greater the result. Detectors therefore usually need to be capable of detecting a wide range of light intensities.

Although luminescence microplates and luminescence microplate readers are of great utility in automated screening, there are a number of critical issues concerned with their use that affect the reliability of their use. A luminescence microplate reader has a series of optical devices wherein each device is positioned to correspond to a well in the microplate that holds a test sample. The optical device is often a photomultiplier tube. In the alternative, the luminescence microplate reader is fitted with a single optical device and the plate, the reading device or both are moved to the appropriate reading position. Use of the microplate on the luminescence microplate reader must involve alignment of each sample well with the optical device of the luminescence microplate reader. Movement of the microplates or optical devices is usually done using stepper motors wherein the movement is guided on a certain number of (factory calibrated) steps from a "home" position. Alignment can be adversely affected when one or more of the aligned components involved is shifted in position or becomes damaged. If, for any reason, the alignment is incorrect, the wells will not be centered properly in alignment with the optical reading device, resulting in an incorrect luminescence measurement. IN addition to optical problems the plate carrier can be physically bent or otherwise misaligned with the original adjustment parameters of the reader which also produces a bad measurement.

The optics used to measure luminescence must avoid detecting transmission of luminescence from one sample well as the luminescence from an adjacent well. This adjacent well detection problem is an alignment problem called "cross-talk". Cross-talk is extremely undesirable because it means the emissions detected, by a particular optical device at a given location originated from the test sample of a different well. In a worse case scenario, a particular well optical device is detecting luminescence cross-talk for all the surrounding or adjacent wells. Depending on where the well is located this can be up to 8 adjacent wells in a standardized microplate set-up. Even in a best worse-case scenario cross talk from a single adjacent well is extremely undesirable.

Linearity is also an important measurement to look at to validate the accuracy of the readings of the luminescence microplate reader. Linearity is a measure of the relationship between different amounts of luminescence emissions in a series of wells as measured by their light output and is usually measured from darkness or close to darkness to saturation of the detector ability to sense light. A linear response relationship should exist between the measured luminescence and the strength of the luminescence emissions. Linearity is an indication of the relative concentration of luminescence emissions in the series of wells. As the optical, electronic and other components of the luminescence microplate reader age, the detection efficiency can be diminished to a lesser or greater degree for some measurements versus others and this seems to be especially the case at the high and low ends of emission measurements. To some extent these problems can be addressed by software programs and by advancing technologies which slow the aging process of the readers. However, these solutions do not solve all the linearity problems with luminescence microplate readers and the need to calibrate the accuracy of the machines remain.

A number of luminescence validity microplates have been developed to accommodate one or more of these problems. For Example in U.S. Pat. No. 6,335,997, there is disclosed a device for testing luminescence microplate readers. It disclosed a means for delivering a series of low level light sources ranging over several orders of magnitude. This is accomplished by shining a light source on a series of fiber optic collection rods where the light for each is attenuated via an opaque sleeve on each rod. Light is delivered to the reader via an output aperture connected to the chamber through drilled tunnels. This construction delivers a means for producing a linearity test. However, the size of the rods and their placement leaves no room for any other type of validity testing on a validity plate of standard size. Further, opaque sleeves can move and easily become unadjusted and change the output of the light conducted to the light output aperture. Another problem is since the fiber optic rods are not directly connected to the light source, the amount of light reaching the far rods can seriously decrease compared with the near in rods, due to both the distance traveled and the interposing other rods. Other luminescence validity microplates are available but all currently suffer from similar problems.

SUMMARY OF THE INVENTION

The present invention relates to a luminescence validity microplate for testing the validity of a luminescence reader comprising a microplate having a plurality of wells with a backlight panel having a fixed light output, positioned behind said wells, said wells consisting of:
  a. a first set of measurement positions in a 3×3 grid suitable for performing a cross-talk one-in-eight test wherein the center position is a well in light emission contact with the backlight panel and the surrounding 8 grid positions do not contain a well or contain a well that is not in light emission contact with the backlight panel;
  b. a second set of measurement positions in a 3×3 grid suitable for performing a cross-talk eight-around-one test wherein the center position does not contain a well or contains a well that is not in light emission contact with the backlight panel and the surrounding 8 positions each contain a well in light emission contact with the backlight panel;
  c. a third set of measurement positions wherein each position consists of a well in light emission contact with the backlight panel and is suitable for performing a linearity test wherein each well of said set is fitted with a neutral density filter of different ability to pass light from the backlight panel or fitted with the same neutral density filter wherein each well in the set is of decreasing diameter;
  d. a fourth set of wells suitable for performing an alignment test wherein each well of the fourth set is the same size and in light emission contact with the backlight panel.

In another aspect of the invention the microplate comprises a luminescence validity microplate having a plurality of wells for testing the validity of a luminescence reader comprising a backlight panel, a light source wherein at least one of said wells is in light emission contact with said panel is modulated by a neutral density filter.

In accordance with the present invention and objectives, a novel luminescence validly microplate (hereinafter referred to as a validity plate) is disclosed. The validity plate of the invention is a microplate wherein the construction is such that the reliability of a luminescence reader may be tested there from. The validity plate is not designed to house a luminescence test sample or for that matter, reagents of any type, rather, it is designed to be fitted with a backlight panel such as a fiber optic or plasma backlight panel, which enables a luminescence reader operator to test the accurate function of the reader. The validity plate contains measurement positions corresponding to the positions normally read by the reader and in the case of a reader which is manufacturer to industry standards to those industry standard positions. Each of the positions on the validity plate comprise either a well that is in light communication with the backlight panel or is either not fitted with a well or wherein the well is not in light communication with the backlight panel.

One embodiment of the backlight panel is a fiber optic backlight panel and can be constructed in a number of ways but in general consists of a woven mesh of fiber optic fibers wherein light enters the panel through the end of the fibers which are exposed to a light emitting diode or other low level light source. The light source such as the LED is selected at a wattage or other measurement criteria such that the light output of the backlight panel is compatible with the light range read by the detector. This could be all the way to the detectors saturation point. Bends in the woven fibers allow the light to be emitted from the edge of the panel and not only is such light low level; it is also essentially even over the entire surface of the panel. These panels have a tremendous advantage over the prior art sources of light used on validity plates which tend to be either very difficult to evenly light, difficult to produce low levels of light, or is so bulky that it is difficult to position more than about 10% of the measurement positions on the validity plate with a luminescence source. While the fiber mesh alone is sufficient, an even better construction consists of a reflective backing, such as Mylar for catching luminescence that is reflected backwards and a diffusion layer on top of the fiber optic layer which further produces an evenly distributed luminescence. The exact amount of luminescence generated by the backlight panel can be varied by either changing the light output of the LED or increasing the number of woven layers in the fiber optic panel or both. Optimally, there are between 1 and 4 fiber optic panel layers used in the practice of the invention. Fiber optic cables are then bundled together and joined, for example, with a ferrule and connected to the remote light source. The light source such as a LED would be normally connected to a battery source, either disposable or rechargeable, and have the extra benefit of having a light source that lasts as long as 100,000 hours before replacement is necessary. These panels can be about any size but in general for the invention would be roughly 70% to 100% the size of the microplate and fit inside the validity plate cavity as will be seen in the later drawings. Typical backlight panels have a light output that depends on the light source but as previously stated will need to be matched to the range of detection of the luminescence reader. So for example, in an embodiment of the invention a fiber optic panel from Lumitex, Inc producers of fiber optic technologies, would be used and further embodiments would include 2 layer and 4 layer fiber optic panels. The panel would be selected or designed to fit inside a validity plate cavity.

Where the amount of luminescence is desired to be varied at a desired measurement position on the validity plate, an individual wells can be fitted with a neutral density filter of selected density. Neutral density filters are thin sheets of grey glass, plastic, crystal or gelatin having plane and parallel faces, of uniform and specific optical density and used for the purpose of reducing the intensity of luminescence from the backlight panel without changing its color. Neutral density filters especially glass or plastic have tremendous advantage over other methods of further producing a variety of luminescence outputs for a validity plate. When combined with the backlight panels of the invention they produce results that are more consistent in luminescence especially when used over several magnitudes of output. Further, they have the benefit of allowing a dose response curve in replicate.

The validity plate of the invention should be constructed of an essentially rigid and durable material and which is light opaque. Such opacity is critical when testing for cross talk. Further, the validity plate is also constructed of a substantially non-reflective surface material and preferably of a black or other very dark color. Embodiments of such preferred material include aluminum, anodized aluminum, Delrin, Kevlar, nylon or polypropylene. In one embodiment, the validity plate consists of an upper plate and a lower plate held together in register via an attachment means such as fastening bolts. The space in-between the two plates forms a cavity in which the backlight panel, battery, light source, battery charger, adjustment pod, or power switch for the battery can be contained. The final size of the validity plate would be the same size as a microplate that would be read on a luminescence reader that is to be validated. The validity plate also would have its validity positions such that they correspond to the measurement positions of the luminescence reader. With the advent of standard microplate sizes, a single validity plate size will now work on most currently made readers. For example, a standardized 96 well luminescence reader would use a validity plate of the standard size read by that reader and have up to 96 measurement positions for validity testing thereon.

A first test provided for on the validity plate of the invention is a test for cross-talk. The construction which enables this test to be carried out comprises two separate sets of measurement positions on the validity plate. A first set of measurement positions establish a one-in-eight well design test and consists of a block of measurement positions corresponding to a 3×3 grid or 9 optical measurement positions on the luminescence reader. The 8 surrounding grid positions either do not contain a well or contains a well that is not in light emission contact with the backlight panel. The single center position consists of a well that is in light communication with the backlight panel. The one-in-eight design test enables the operator to test if a single well is cross-talking with one of its neighbor positions. In an ideal luminescence reader situation, the outer eight positions would read zero luminescence from the center luminescence well (after adjustment for background luminescence). Any reading above a background reading would indicate cross-talk. The validity plate also would enable the user to determine background levels by reading the validity plate at positions with no luminescence communication and with no wells surrounding the measurement position in such communication.

The second cross-talk test provided for on the validity plate of the invention is a second set of measurement positions that establish an eight-around-one design. It consists of the same 3×3 grid of measurement positions again corresponding to 9 measurement positions on a luminescence reader. This test however provides an opposite construction to the previous test. The exterior 8 positions consist of the wells on the validity plate in light communication with the backlight panel and the center position having no light communication therewith. This set of measurement positions tests for a "worse" case cross talk situation wherein the center measurement position of the grid, which under ideal reading conditions should have a second reading (after background), will have some reading above that level if there is cross-talk from any or all of the surrounding measurement positions. Background is likewise determined as previously described.

The second test provided for by the specific construction of the validity plate of the invention relates to a measurement of the linearity of the relationship between the luminescence emissions on the validity plate with the result produced on a luminescence reader. To test for linearity, a plurality of wells in light communication or contact with the backlight panel and each provided with a different neutral density filter are provided for the validity plate. It is preferable for the test that there is a mathematical relationship between each successive cell such that a curve can be generated over a predictable linear range of luminescence output, i.e. measurements of the light of the validity plate by the reader will graph to a straight line. So, for example, in one embodiment, each successive well's neutral density filter varies by a factor of 10 to the preceding well so that when read by the reader a linear curve may be produce for a properly operating reader. In another embodiment, there is a plurality of rows of linearly related wells. For example, 4 rows where there are 8 wells in each, in other words 4 linear test rows.

Since there is both a different light output and a mathematical linear relationship between wells, only if the luminescence reader is operating properly, will the resulting measurements produce a linear curve. In a particular embodiment of the invention, there are 8 measurement positions wherein the first and last measurement positions differ by a factor of 8 and wherein each adjacent position differs by a factor. Such relationship could be plotted in linear fashion due to the relationship between adjacent measurement positions.

Valid readings produce a straight line when plotted as a standard dose response curve, while an error in reading shows up as a deviation in the otherwise smooth linear curve. While the 8 positions produce a curve, more or less measurement positions for a linearity test can be used as desired and within the skill of the user. An advantage of multiple copies of the linearity test is that the average of the measured values can be plotted and the so-called $R^2$ value of a linear regression calculation must be higher than a predetermined threshold of the reader to acceptably pass the linearity test.

The fourth test provided for by the construction of the validity plate is one that tests for proper alignment of the microplate relative to the optical reading positions of the luminescence reader and measures alignment of the luminescence reader. A minimum of 4 wells is positioned such that readings taken together will produce readings that indicate any misalignment in either x, y or z axis readings. For this purpose one embodiment comprises a set of wells at or near at least two edges (either the short or long edges of the rectangle) of the microplate are each of the same diameter (usually less than that normally used on microplates on the particular reader, for example ½). Each is in emission light communication or contact with the backlight panel and thus each measurement well or position emits the same amount of light. In one embodiment, the two edges are opposite edges of the microplate (i.e. left and right edges or top and bottom edges). Deviation of the readings of this set of wells or positions can be attributed to reader measurement alignment problems in 3 dimensions. In one embodiment, these wells are smaller than normal well size e.g. ½ size and could further comprise and entire column or row of well positions for the reader. So for example, in a 96 well position luminescence reader, a first column of 8 well positions corresponding to column one on the reader and a second column of 8 positions corresponding to the last column positions on the reader is used. In this, case each of the well positions will give the same luminescence reading if the alignment is correct for the reader. Other combinations of test wells would be useful from this disclosure such as for example 4 corners.

A final test possible with the validity plate of the invention is reproducibility verification. This is done by measuring the validity plate multiple times with the reader to be evaluated and performing a standard statistical evaluation of the results expected based on the luminescence of the backlight panel.

DESCRIPTION OF EMBODIMENTS OF THE INVENTION

Figure 1:
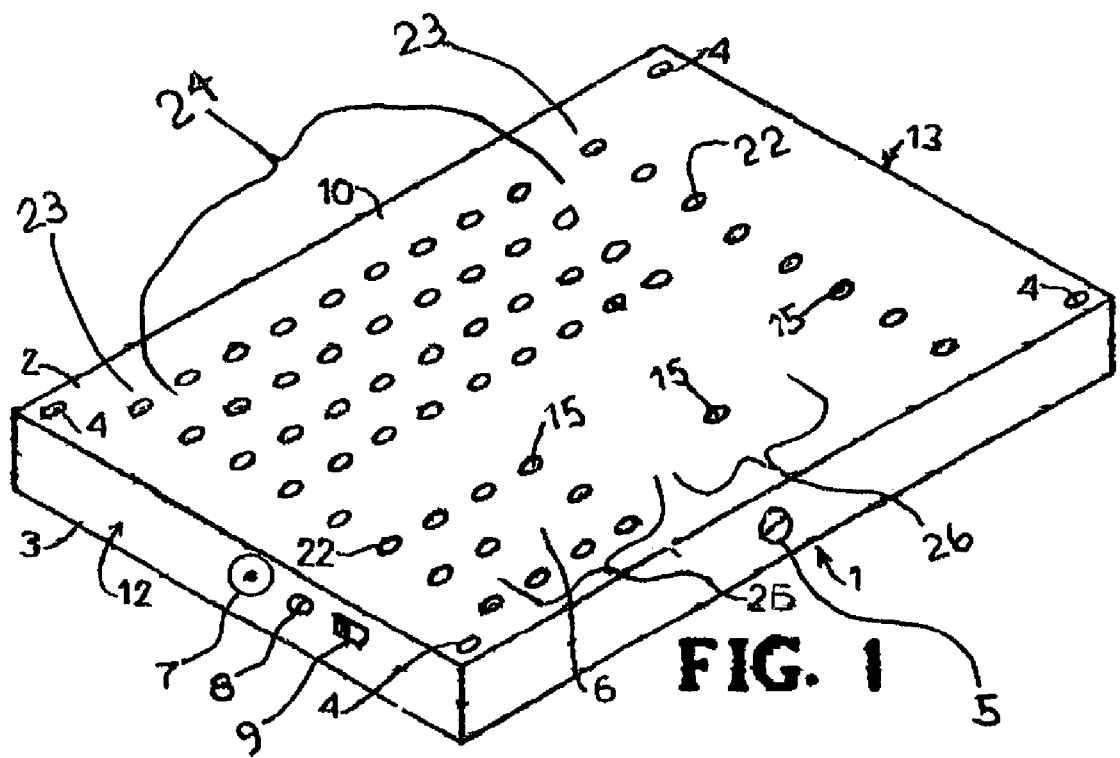
FIG. 1 is a perspective view of an embodiment of the present invention depicting a fluorescence validation microplate of the invention.

Referring to the figures, FIG. 1 is a perspective view of an embodiment of the present invention. The validity plate 1, depicted, is one for testing a 96 position luminescence microplate reader. It consists of a top plate 2 and a bottom plate 3 (not seen in this perspective but see FIGS. 3 and 4 on the bottom side of the validity plate 1) connected with bolts 4 which can be used such that they are screwed in from the top plate 2 as seen in this perspective or screwed in through the bottom plate 3 as seen in FIG. 4. The top surface 10 of the top plate 2 is indicated as well as the left side 12 having the charger port 7, indicator light 8 and on/off switch 9 and the right side 13 of the top plate 2 for orientation purposes. Note also backlight intensity adjustment potentiometer 5 on the facing side 43 of top plate 2.

The validity plate 1 has wells 22 which can either be of the diameter normally read by the luminescence microplate reader the validity plate 1 is to be used on or vary in diameter (such as the top to bottom column of wells 23 which while depicted as the same diameter as the other wells can, in one embodiment, be ½ diameter or the other wells on the validity plate 1). Each well is drilled in such a way that the fiber optic backlight panel 15 can be seen at the bottom of any well 22. The fiber optic backlight panel 15 is positioned in between top plate 2 and bottom plate 3 in a cavity between the two and positioned such that it can shine light out of each of the wells 22 of the validity plate 1. The validity plate 1 also has blank measurement positions 6 wherein there is no optical connection to the optical fiber backlight panel 15. In the embodiment shown there is just no well 22, however it would also be possible to have a well that is plugged to block light from the backlight panel 15 in any method suitable and known in the art. Taking both the wells 22 and blank 6 measurement positions together they would correspond to the luminescence microplate reader's optical measurement positions, in the shown example a total of 96 measurement positions. In the embodiment shown in the figures there are fifty-six wells 22 and forty-two blanks 6. The series of linearity wells 24 are a series of 4 rows of 8 wells giving in this example 4 redundant linearity tests. For the linearity wells 24 there are placed a series of eight neutral density filters for each row in-between the backlight panel 15 and the top plate 2 to vary linearly the light output of the backlight panel 15. The eight-around-one 25 series of eight wells 22 and one blank 6 are shown as is the one-in-eight 26 series of eight blanks 6 and one well 22.

Figure 2:
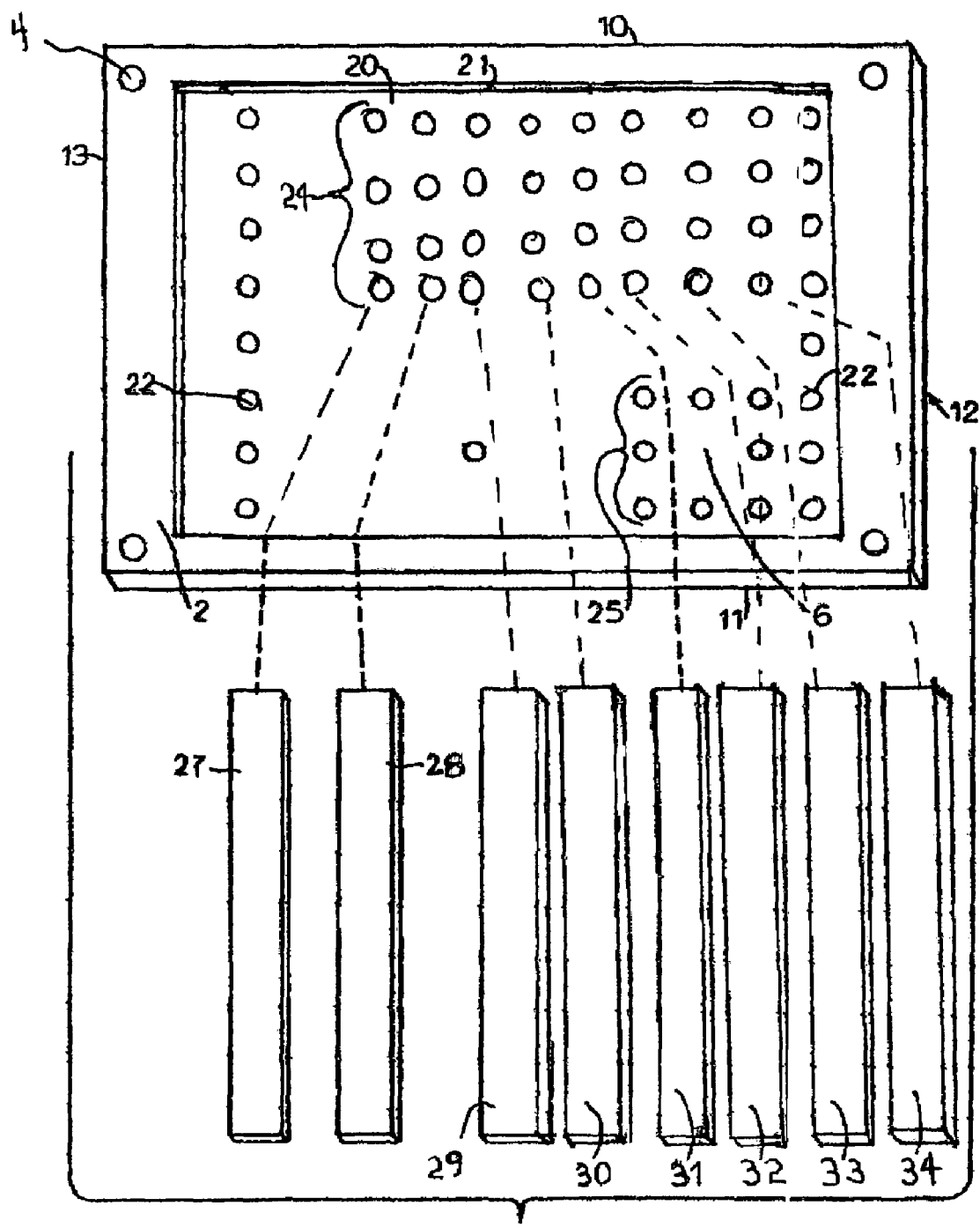
FIG. 2 is a perspective view of the bottom surface of the top plate of the validity plate in position to receive the illustrated neutral density filters.

FIG. 2 depicts a bottom view of the top plate 2 of a validity plate 1 of the invention which has been separated from the bottom plate 3 shown in FIG. 4. It can be seen that all the wells 22 extend through the top plate 2. The neutral density filters 27, 28, 29, 30, 31, 32, 33 and 34 are positioned against the bottom side of the linearity test wells 24 such that they will be between the reader and the backlight panel. FIG. 2 also indicates the center section of the top plate 2 containing all 96 measurement positions has been hollowed out to create a cavity 20 of thickness 21 which is about 80% of the thickness of the top plate 2. The bottom plate 3 can fit into the cavity such that the thickness of the Validity plate 1 is the same as that of the top plate 2 or it can be screwed in such a manner that the total thickness of the validity plate 1 is the combination of the top plate 2 and bottom plate 3.

Figure 3:
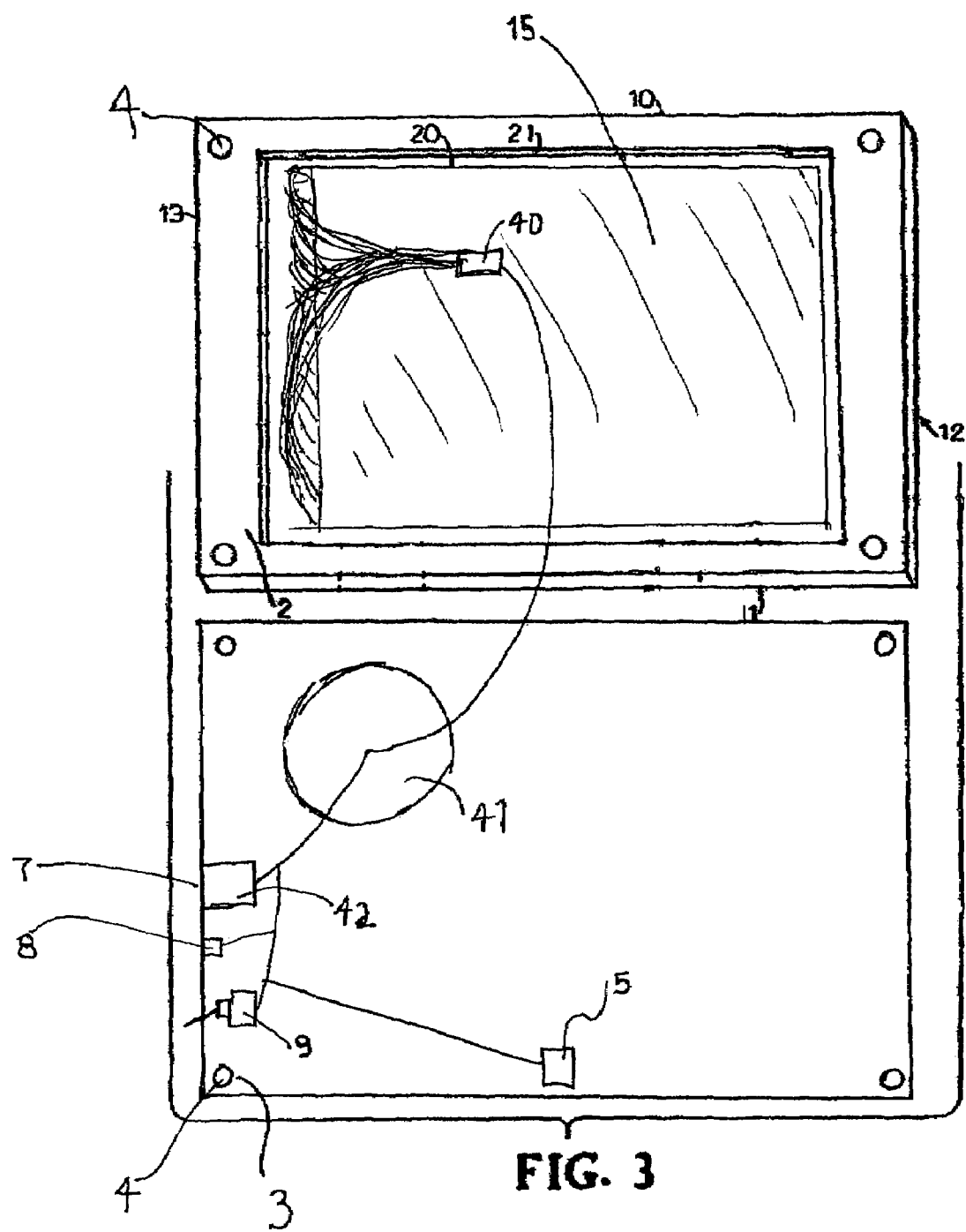
FIG. 3 is an exploded perspective view of the bottom surface of the top plate and the inside surface of the bottom plate of the validity plate showing the positioning of the backlight panel, the light source, battery, switches, adjustment pod and charging unit.
Figure 4:
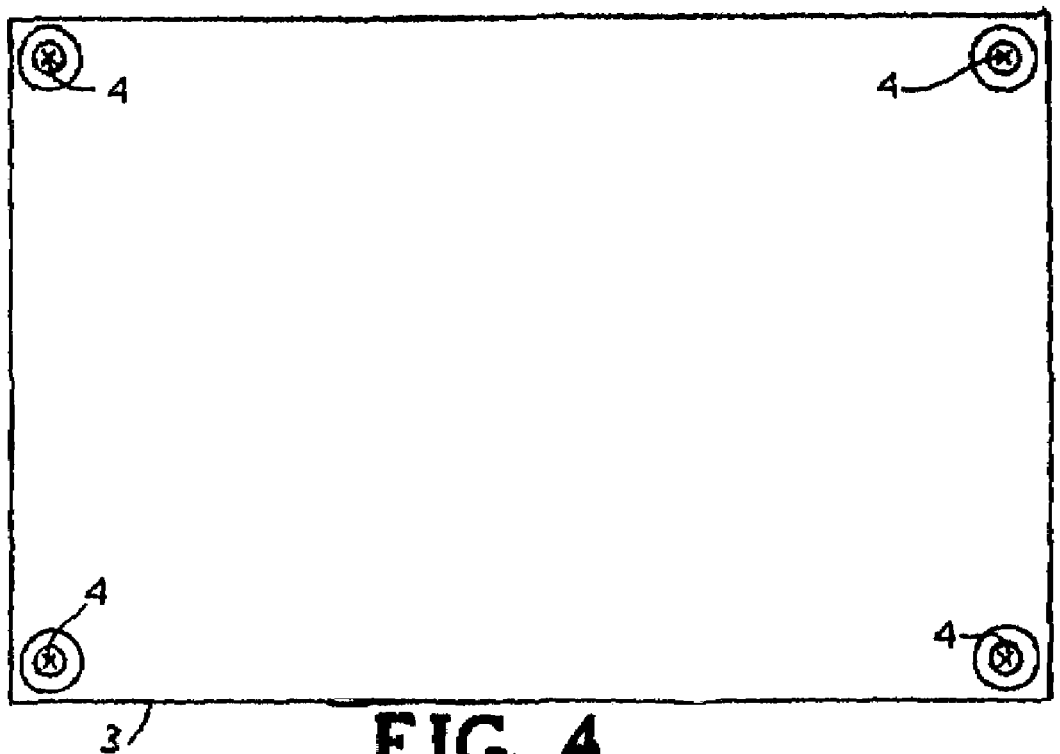
FIG. 4 is a bottom view of the bottom plate of the validity plate of the invention inside.

FIG. 3 is an exploded perspective view of top plate 2 as well as the inside view of bottom plate 3. The fiber optic backlight panel 15 extends over all measurement positions (the wells 22 and blanks 6), with light source 40, battery 41, and battery charger 42. As can be seen from the drawings the fiber optic backlight panel 15 is positioned in the cavity 20 and since the fiber optic fibers can bend, the light source can be positioned just about anywhere in the cavity 20. The remaining components i.e. battery 41 and battery charger 42 are mounted on the inside of the bottom plate 3 in this embodiment. All the components are wired to the appropriate charger port 7, indicator light 8, on/off switch 9, potentiometer 5 and the like by means known in the art.

Lastly, FIG. 4 is a bottom view of the bottom plate 3 of the validity plate 1 of the invention. It is solid except for the bolt 4 holes for connecting top plate 2 to bottom plate 3.

The above embodiments are representative only and not intended to be limiting. Varying choices of material, filter densities, and the like are within the skill in the art and therefore included and contemplated in the scope of this invention.

I claim:

1. A luminescence validation microplate for testing the validity of a luminescence microplate reader comprising a microplate having a plurality of wells with a backlight panel having a fixed light output, positioned behind said wells, said wells consisting of:
   a) a first set of measurement positions in a 3×3 grid suitable for performing a cross-talk one-in-eight test wherein the center position is a well in light emission contact with the backlight panel and the surrounding 8 grid positions do not contain a well or contain a well that is not in light emission contact with the backlight panel;
   b) a second set of measurement positions in a 3×3 grid suitable for performing a cross-talk eight-around-one test wherein the center position does not contain a well or contains a well that is not in light emission contact with the backlight panel and the surrounding 8 positions each contain a well in light emission contact with the backlight panel;
   c) a third set of measurement positions wherein each position consists of a well in light emission contact with the backlight panel and is suitable for performing a linearity test wherein each well of said set is fitted with a neutral density filter of different ability to pass light from the backlight panel or fitted with the same neutral density filter wherein each well in the set is of decreasing diameter;

d) a fourth set of wells suitable for performing an alignment test wherein each well of the fourth set is the same size and in light emission contact with the backlight panel.

2. A microplate according to claim 1, wherein the third set of said wells consist of four separate sets of eight wells, wherein within each set the wells are fitted with a neutral density filter of a different light filtering capacity.

3. A microplate according to claim 1 wherein said fourth set of wells consists of two rows of eight wells in each row positioned at opposite sides of the microplate.

4. A microplate according to claim 1 wherein the neutral density filter is plastic or glass.

5. A microplate according to claim 1 which is designed to be used to validate a 96 well luminescence microplate reader.

6. A microplate according to claim 1 comprising a rechargeable power source for the fiber optic backlight panel.

7. A microplate according to claim 1 wherein the fiberoptic backlight panel comprises a reflective backing, two to four lawyers of woven fiber optic material and a top light diffusion layer.

8. A microplate according to claim 1 wherein the backlight panel is a fiber optic backlight panel.

* * * * *